(12) United States Patent
Martin et al.

(10) Patent No.: US 7,904,251 B2
(45) Date of Patent: Mar. 8, 2011

(54) METHOD FOR MODIFICATION OF A SYNTHETICALLY GENERATED ASSAY USING MEASURED WHOLE CRUDE PROPERTIES

(75) Inventors: Gregory M. Martin, Centreville, VA (US); James M. Brown, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 813 days.

(21) Appl. No.: 11/327,790

(22) Filed: Jan. 6, 2006

(65) Prior Publication Data

US 2006/0160137 A1    Jul. 20, 2006

Related U.S. Application Data

(60) Provisional application No. 60/644,908, filed on Jan. 19, 2005.

(51) Int. Cl.
  *C40B 30/02*   (2006.01)
(52) U.S. Cl. .......... 702/22; 702/25; 702/30; 250/339.12; 436/29; 703/2

(58) Field of Classification Search .............. 702/22–26, 702/30; 703/2; 250/339.09, 339.12; 436/29–30
See application file for complete search history.

(56) References Cited

U.S. PATENT DOCUMENTS

| 5,348,645 | A | * | 9/1994 | Maggard et al. .............. 208/209 |
| 5,699,269 | A |   | 12/1997 | Ashe et al. |
| 6,662,116 | B2 |  | 12/2003 | Brown |

OTHER PUBLICATIONS

Sales brochure of the Crude Oil Assay Simulator (Assay-Sim) and Crude Cut Predictor (CCPP) Models from HPI Consultants (public availability date Dec. 20, 2003; Download date Jul. 30, 2009).*

* cited by examiner

*Primary Examiner* — Robert J Hill, Jr.
*Assistant Examiner* — Brian McCaig (57) ABSTRACT

The present invention is a method for modifying any synthetically generated assay of a whole crude oil or a portion of a whole crude, such as a condensate or resid material, by using measured crude properties. These measured properties are used to adjust the synthesized assay values to obtain a more accurate representation of the unknown hydrocarbon material.

6 Claims, 4 Drawing Sheets

Figure 1

Figure 2
Nitrogen VA Distribution Comparison - Ob River Light

Figure 4
Sulfur VA Distribution Comparison - Mondo

METHOD FOR MODIFICATION OF A SYNTHETICALLY GENERATED ASSAY USING MEASURED WHOLE CRUDE PROPERTIES

This application claims the benefit of U.S. Provisional application 60/644,908 filed Jan. 19, 2005.

BACKGROUND OF THE INVENTION

The present invention relates to modifying a synthetically generated assay. In particular, the modification is done by using whole crude properties.

Within the petrochemical industry, there are many instances where a very detailed analysis of a process feed or distillation product is needed for the purpose of making business decisions, planning, controlling and optimizing operations and certifying products. Such a detailed analysis will be referred to as an assay, a wet crude oil assay being one specific example. Since a detailed assay is both costly and time consuming to perform, it is desirable to have a surrogate methodology that can provide the information of the detailed analysis inexpensively and in a timely fashion. Techniques such as those involving NMR, UV, visible and near and mid infrared spectroscopy can provide information of varying degrees of detail, inexpensively and in a timely fashion. This information can then be used to synthesis an estimate of the detailed assay, the Virtual Assay.

The quality of the predictions of the various assay properties made using these Virtual Assay synthesis techniques can vary considerably as a function of the specific analytical technique employed to generate the Virtual Assay as well as the quality, scope and specific blend of reference materials that are used. For example, various forms of NMR, near, or mid range IR spectroscopies are sensitive to particular types of molecules or molecular functional groups. Thus these spectroscopies can provide information on certain molecules or molecular types, but they do not directly measure such properties as molecular weight or boiling point, nor are they sensitive to trace level elements such as metals (e.g. Ni, V or Fe) or trace level species (e.g. mercaptans).

Therefore, predictions of the level of these properties, elements or compounds can be less accurate and is simply a function of the surrogate selected or blends of reference materials used to match the spectra and other key measured properties. The reference materials used to generate the blend also determine the accuracy of the blend. If the blend is comprised of materials which are very similar to the target material being analyzed, based on similar geological, chemical formulations or physical location, then the accuracy of the prediction may be sufficient to meet the required business objectives. However, if the blend is comprised of materials, which are substantially different than the target material being analyzed, then the prediction of these properties could vary significantly from the actual levels present in the target material.

Therefore, an ability to improve the Virtual Assay prediction made based on these analytical techniques would be extremely valuable to making better business decisions. The current invention provides such an improved ability.

Current state of the art as reported in the literature, includes but is not limited to analytical techniques involving NMR, UV, visible and near mid infrared spectroscopy. Examples include:

Infrared and Raman spectroscopies have been employed for process analysis of a variety of petrochemical streams. G. M. Hieftje, D. E. Honigs and T. B. Hirschfeld (U.S. Pat. No. 4,800,279 Jan. 24, 1989) described the prediction of physical properties for simple hydrocarbon mixtures from near-infrared (NIR) spectra using multiple linear regression (MLR). D. A. Swinkels, P. M. Fredricks and P. R. Osborn applied FT-IR and Principal Components Regression (PCR) to the analysis of coals (U.S. Pat. No. 4,701,838 Oct. 20, 1987). J. M. Brown (U.S. Pat. No. 5,121,337 Jun. 9, 1992) describes a method for predicting property and composition data of samples using spectra and Constrained Principal Spectra Analysis (CPSA). R. Clarke describes a method for measuring properties of hydrocarbons using Raman spectroscopy (U.S. Pat. No. 5,139,334 Aug. 18, 1992). R. H. Clarke and D. Tang describe a method and mid-infrared apparatus for determining hydrocarbon fuel properties (U.S. Pat. No. 5,225,679 Jul. 6, 1993). D. C. Lambert and A. Martens (EP 2852521 and U.S. Pat. No. 5,490,085 Feb. 6, 1996) describe the prediction of octane number using NIR spectra and MLR, as does S. M. Maggard (U.S. Pat. No. 4,963,745 Oct. 16, 1990). Maggard also describes the estimation of paraffins, isoparaffins, aromatics, naphthenes and olefins in gasolines using NIR and MLR or Partial Least Squares (PLS) (U.S. Pat. No. 5,349,188 Sep. 20, 1994), the prediction of blend properties from the spectra of blend components using NIR and MLR (U.S. Pat. No. 5,223, 714 Jun. 29, 1993), and the prediction of oxygenates and oxygen content of gasolines using NIR spectra. S. Maggard and W. T. Welch discuss prediction of organic sulfur content for mid-distillate fuels using NIR spectra (U.S. Pat. No. 5,348,645 Sep. 20, 1994). J. B. Cooper, M. B. Sumner; W. T. Welch and K. L Wise describe a method for measuring oxygen and oxygenate content of gasolines using Raman spectroscopy (U.S. Pat. No. 5,596,196 Feb. 21, 1997). R. R. Bledsoe, J. B. Cooper, M. B. Sumner; W. T. Welch, B. K. Wilt and K. L. Wise describe a method of predicting octane number and Reid vapor pressure of gasolines using Raman spectroscopy (U.S. Pat. No. 5,892,228 Apr. 6, 1999). These methods typically involve linear models for individual properties, and are thus not necessarily useful for properties that are nonlinear functions of composition, nor for prediction of properties of subfractions of the sample being analyzed. While they can provide rapid analyses on minimal sample volumes, their application for detailed analyses would require the development and maintenance of an impracticably large number of models. In addition, many of these NIR methods operate in spectral regions where crude oil is essentially opaque. Raman methods are typically not applicable to crude oils or other heavy hydrocarbons due to interferences from fluorescence.

Espinosa, A. Martens, G. Ventron, D. C. Lambert and A. Pasquier (EP 305090 and U.S. Pat. No. 5,475,612 Dec. 12, 1995) describe predicting physical properties of blends from near-infrared spectra of blend components using MLR. Products and ratios of absorbances were included in an attempt to predict nonlinear properties such as RON. A. Espinosa, D. C. Lambert, A. Martens and G. Ventron (EP 304232 and U.S. Pat. No. 5,452,232 Apr. 25, 1990) describe a method for predicting properties of process products from spectra of process feeds using NIR and MLR. Products and ratios of absorbances were again used to handle nonlinear properties. B. N. Perry and J. M. Brown describe a method for improving the prediction of nonlinear properties by post-processing results from linear models (U.S. Pat. No. 5,641,962 Jun. 24, 1997). J. M. Tolchard and A. Boyd (WO9417391) describe the use of NIR and neural networks for the prediction of hydrocarbon physical properties. While these methods could potentially be use to predict properties that have nonlinear relationships to composition, all would require that separate models be built for each property to be predicted, and are thus impractical for assay synthesis.

R. DiFoggio, M. Sadhukhan and M. Ranc (U.S. Pat. No. 5,360,972 Nov. 1, 1994) describe a method for estimating physical properties of a material using a combination of infrared data and data indicative of trace level compounds. DiFoggio et. al. do not teach the use of infrared and inspection data, and their method would require separate models to be built for each property to be estimated.

Other methodologies have been employed for detailed analyses of hydrocarbons. T. R. Ashe, R. W. Kapala and G. Roussis (U.S. Pat. No. 5,699,270 Dec. 16, 1997) employed PLS models of GC/MS data to predict chemical, performance, perceptual and physical properties of feed and product streams from various steps in lubricating oil manufacturing. T. R. Ashe, S. G. Roussis, J. W. Fedora, G. Felshy and W. P. Fitzgerald (U.S. Pat. No. 5,699,269 Dec. 16, 1997) used PLS models of GC/MS data to predict physical and chemical properties of crude oils. Both method employed separate models for each property predicted.

I. H. Cho, J. G. Choi and H. I. Chung (WO 00/39561) described an apparatus that combined a distillation unit and a spectrometer for analysis of crude oils. Separate chemometric models were employed for each property for each distillate cut.

K. Hidajat and S. M. Chong claim to measure total boiling point and density of crude oils from NIR spectra (*J. Near Infrared Spectroscopy* 8, 53-59 (2000)). Neither other whole crude properties, nor properties of distillate cuts were predicted.

PROCESS MRA by Invensys—R. W. Karg and T. A. Clinkscales (WO 01/51588) describe a method for using NMR to control a petroleum distillation process. R. W. Karg and T. A. Clinkscales and C. Swart (WO 01/70912) describe a method of using NMR to control crude blending. Neither method provides a complete synthetic assay. In particular, the methods do not describe the prediction of sulfur, acid number, metal content or trace components.

TOPNIR by Intertek/CalebBrett—B. Descales, D. Lambert, J. LLinas, A. Martens, S. Osta, M. Sanchez and S. Bages (U.S. Pat. No. 6,070,128 May 30, 2000) describe a topology based method for determining properties from NIR spectra. Their method calculates an Euclidean distance between the spectrum of the sample being analyzed and all of the reference spectra in the database. Reference samples whose spectra fall within a predetermined distance of the unknown spectra are selected, and the properties of the unknown are calculated as the average of the properties of the selected references. Alternatively, the spectrum of the unknown can be fit as a linear combination of the selected references, and the properties of the unknown calculated as the weighted combination of the reference sample properties. Nonlinear properties are handled through blending factors. If there are insufficient references within the predetermined distance of the unknown, the method provides a means of densifying the database to interpolate between the reference samples. While the method of Descales, et. al. can be used to analyze the unknown as if it were a blend of the reference samples, the blend components are limited to those samples who have spectra nearly identical to the spectrum of the unknown, i.e. the nearest neighbors in the spectral space.

Petrobras NIR—A. F. Bueno described the use of NIR for crude oil characterization (http://www.sbqclaq.sbq.org.br/celio/pdf/Aerenton.pdf, Pittsburgh Conference 2004, paper 20600-300). Only distillation and a limited number of physical properties were predicted.

Various of these techniques could be used to generate some or all of the data for a synthesized assay which is the starting point for the application of the methodology of this invention.

However, the preferred method of generating a Virtual Assay is the technique described by J. M. Brown, U.S. Pat. No. 6,662,116 B2, Dec. 9, 2003, "Method for Analyzing an Unknown Material as a Blend of Known Materials Calculated so as to Match Certain Analytical Data and Predicting Properties of the Unknown Based on the Calculated Blend" (hereinafter referred to a "EM virtual assay").

Some of these techniques either select the closest match based on a set of predetermined criteria from a library of crude oils, or develop a blend of materials, which match the infrared spectra, and other key measured properties in the case of the Brown U.S. Pat. No. 6,662,116. The calculated blend of the reference materials is then used to predict additional chemical and physical properties of the unknown using the measured chemical and physical properties of the reference materials and known blending relationships.

None of these existing techniques have used directly measured property values to adjust the predicted or blended whole crude and distributed values resulting from the analytical tests that this invention covers.

SUMMARY OF THE INVENTION

The present invention is a method for modifying any synthetically generated assay of a whole crude oil or a portion of a whole crude, such as a condensate or resid material, by using measured crude properties. These measured properties are used to adjust the synthesized assay values to obtain a more accurate representation of the unknown hydrocarbon material. The synthetically generated assay can be formulated by using a number of analytical techniques. These analytical techniques are typically used to either select a surrogate crude based on closest match criteria, or to calculate a blend of reference materials to predict chemical, physical, and performance properties for the unknown target material. Any synthetically generated assay developed by these techniques are referred to wherein as a Virtual Assay.

Current limitations of these Virtual assay synthesis techniques, either those which select a closest match or generates a blend of assays, is that only certain properties or qualities can be selected for determining the closest match, or for use as optimization targets when determining a blend of crude oils. However, different properties can be critical to different refineries depending upon their equipment configuration, availability or product specifications. So while one refinery may be limited by total sulfur in the crude or a particular distillate stream, another refinery may have a limitation on neutralization number in the atmospheric resid. Therefore, different levels of accuracy for different properties and for different refineries are expected. Not all properties generated by a Virtual Assay are predicted with the same level of accuracy.

The present invention is a methodology for modifying the Virtual Assay predicted whole crude and distributed properties (properties as a function of boiling point) to obtain a more accurate representation of the crude quality. The invention includes steps to determine which whole crude properties are critical to measure for a given target sample, the distribution priorities that should be followed, a procedure for modifying the values and adjusting the distributed properties accordingly and ensuring the final modified synthetic assay is in material balance.

The crude for which the assay is being generated is wherein referred to as the target crude. This invention involves first determining which whole crude properties to measure for the target crude. This is a function of which properties for the target crude are present at sufficient levels to be critical, which refineries would be processing the target crude and the processing limitations of these refineries. The selected whole crude properties are tested by the generally accepted analytical testing procedures, such as ASTM methods or proprietary techniques. The target crude Virtual Assay is then loaded into an assay workup tool. The assay workup tool is designed to take laboratory data and generate a complete finished assay. At this point, assuming the values for the properties measured for the target crude sample differ from those same properties predicted from the Virtual Assay, the Virtual Assay values are modified to match the measured values, and the property distribution as a function of boiling point is adjusted accordingly.

Using an assay workup tool, a surrogate assay, which exhibits similar characteristics to the target crude, is selected. The ideal surrogate is an assay based on the same crude oil grade. An alternative choice is a crude oil of similar characteristics, exhibiting similar qualities and property distributions. The surrogate is loaded into the assay workup tool. The property distribution of the surrogate assay are overlaid on the target assay, and scaled such that the overall property value matches the measured target value and the property distribution is similar to the surrogate assay.

This methodology provides an accurate value of the whole crude property as well as an improved distributed property characterization of the target crude which can be used as any other crude assay for a variety of business purposes.

The steps of the method of the present invention include generating a synthetic assay for a material, measuring one or more critical property of the material, selecting a surrogate assay for each of the critical properties to provide a property distribution for each critical property, calculating a material balanced value for each critical property, adjusting the property distribution for the surrogate assay such that the material balanced property values equal the measured property values for each critical property, and replacing the property distribution of the synthetic assay with the adjusted property distribution of step (e).

The steps of the method of the present invention include generating a synthetic assay for a material, measuring one or more critical property of the material, selecting a surrogate assay for each of the critical properties to provide a property distribution for each critical property, calculating a material balanced value for each critical property, adjusting the property distribution for the surrogate assay such that the material balanced property values equal the measured property values for each critical property, and replacing the property distribution of the synthetic assay with the adjusted property distribution of step (e).

In a preferred embodiment, the material is a crude oil, a condensate or a resid and the synthetic assay is generated by EM Virtual Assay.

DETAILED DESCRIPTION OF THE PREFERRED EMBODIMENTS

Within the petrochemical industry, there are many instances where a very detailed analysis of a process feed or product is needed for the purpose of making business decisions for planning, controlling and optimizing operations, and certifying products. The methodology used in the detailed analysis which is typically known as a wet crude assay, is costly and time consuming to perform, and is not amenable to real time analysis. A wet crude oil assay can take from several weeks to several months to complete.

The recommended assay terminology is typically applied to a wet crude oil assay that is felt to be fairly representative of current quality of a specific grade of crude oil. It is well established and a recognized fact in industry that variation in crude oil quality occurs. Most in industry select a wet assay which is felt to be representative and typical of the quality which might be expected for the specific grade of crude oil, and use this assay data for making operations decisions when this grade of crude oil is being purchased and refined. This wet assay is assumed to represent a typical crude oil cargo sample and is typically referred to as a "recommended assay".

In many instances, if the variation in crude oil quality is large, the recommended assay may not be representative of current cargoes, and its use may lead to inaccurate business decisions. Additionally, as new crude grades become available, there may be opportunities to purchase these before a wet assay can be undertaken. In such instances, it is desirable to an alternative means of estimating assay data on current and potential cargoes.

Historically, if a wet assay is unavailable, it has been customary to select a surrogate crude to represent the grade being processed. The selection was typically made based on known geochemical similarities, and limited whole crude measurements. More recently, alternate methodologies have been described that generate information similar to that of the detailed analysis in less expensive and more timely fashion. As described above, various attempts have been made to correlate assay properties to NMR and infrared spectra and to GC/MS data. While these correlation methods do not calculate all of the properties measured in a wet assay, the predicted properties for an unknown crude could be used as the basis for the selection of a surrogate. The methods of B. Descales, D. Lambert, J. LLinas, A. Martens, S. Osta, M. Sanchez and S. Bages (U.S. Pat. No. 6,070,128 May 30, 2000) and J. M. Brown, (U.S. Pat. No. 6,662,116 B2, Dec. 9, 2003) are capable of predicting a complete synthetic assay either by selecting the closest match in a library of FT-NIR crude oil spectra, or by developing a blend of crudes to match the FT-MIR spectra, and other key measured properties. However, the accuracy of the physical and chemical characterizations produced by these methods are not always comparable to that of the measured wet assay.

While these techniques can be employed to optimize the match of the target sample to the closest match or blend, not all properties can be matched with the same level of accuracy. Therefore, many critical property predictions could be improved by an alternate method of developing these values.

The data derived from these analyses will typically be stored in an electronic database where it can be mathematically manipulated in an assay work-up tool to estimate crude qualities for any desired distillation range. For example, commercial crude assay libraries are available from Haverly Systems Inc., and HPI Consultants Inc., both of which provide tools for manipulating the data, as does Aspentech Inc. Assay data is published by Crude Quality Inc., by Shell Oil Company, and by Statoil. The property versus distillation temperature data is typically fit to smooth curves that can then be used to estimate the property for any desired distillation cut.

The present invention is applicable to improving the prediction accuracy of the chemical, physical, and performance properties of crude oils as well as petrochemical and product streams. The present invention uses the prediction of the blended whole crude properties based upon the multivariate analytical technique described by Brown or other such techniques that produce a completed assay referred to as a Virtual Assay and further describes a methodology for modifying predicted whole crude and distributed properties generated by the alternative analytical techniques described above to obtain a more accurate crude analysis.

The invention may also include the steps:
  Determining which whole crude properties are critical to measure for a given target sample
  Determining distribution value priorities that should be followed
  Adjusting the distributed properties accordingly
  Ensuring the final modified blended assay is in material balance.

Significant Economic Advantages can be Realized

The values of particular properties for a given grade of crude oil are important for a number of reasons. Some refinery the performance of processing units such reformers, hydrotreaters, catalytic crackers can be limited by total amounts of nitrogen, sulfur, Conradson carbon or metals levels in their feeds. Therefore, not only are the whole crude properties of interest, but how those properties are distributed through the boiling range of the material are critical. Whole crude sulfur may vary between less than 0.01 wt % to over 5.0 wt %. Nitrogen content can vary between less than 1 ppm to over 8000 ppm, while Conrad son carbon can range between 0 and over 15%. One might expect these values to only be of significance to a refinery if they exceed the refinery's operational envelope. However, they can also be critical if a refinery is attempting to purchase a feed of lower sulfur or nitrogen to balance a crude oil they have already obtained which is higher than their operational limits would permit. As an example, a refinery may have a limit of 500 ppm sulfur in their diesel. They may have a crude oil which if processed alone through their processing units would result in a diesel suflur of 650 ppm. Therefore, they would seek to purchase a crude oil with a lower sulfur content to blend with the higher sulfur crude to balance the resulting sulfur levels and obtain their 500 ppm target. Therefore, sulfur levels which could vary by only a seemingly insignificant 100 to 200 ppm in the diesel range, in actuality can have a substantial economic impact on the refinery's operations. Crude values vary significantly as a function of key qualities such as gravity, sulfur, neutralization number, con carbon and nitrogen as examples. Potential price differentials that can vary between 0.25 $/B to 0.75 $/B or more can exist between crude oils as a function of their seemingly similar sulfur properties. When cargoes consisting of 500,000 barrels in a single purchase are considered, this can result in an economic delta of $125,000 to $375,000 on a single crude purchase. When multiple cargoes are typically purchased weekly, significant yearly economic incentives can be realized with a more accurate representation of a crude oils' quality distribution.

Determining which Whole Crude Properties are Critical to Measure for a Given Target Sample The invention first requires a determination of which whole crude properties should be measured. This determination is based on the absolute level of the property generated by the blend, the inherent accuracy of the prediction and this property's criticality for the intended business use. The property's criticality can vary as a function of the specific business application, or the refinery configuration and operating limitations. Table 1 identifies the typical whole crude tests that are conducted on a wet whole crude assay. Other properties measured by industry accepted tests could also be adjusted based on the approach outlined in this invention.

TABLE 1

| Sample | Possible Analyses | Method |
|---|---|---|
| Whole Crude | API Gravity, Specific Gravity and/or density | ASTM D287, D4052, D5002 |
| | Fe, V, Ni, Na | ICP-AES |
| | Nitrogen | ASTM D4629 |
| | Basic Nitrogen | UOP 269 |
| | Sulfur | ASTM D2622, D4294, or D5453 |
| | Hydrogen sulfide | ASTM D3227 |
| | Mercaptan Sulfur | ASTM D3227 |
| | Aliphatic Sulfur | |
| | Volume % and Weight % Yields | ASTM D2892 and D5236 |
| | Simulated Distillation | ASTM D5307 |
| | Neutralization Number | ASTM D664 |
| | Pour Point | ASTM D97, D5853 or D5950 |
| | Freeze Point | ASTM D2386 |
| | Cloud Point | ASTM D2500, D5772 |
| | Reid Vapor Pressure | ASTM D323 |
| | Sediment and Water | ASTM D1796 |
| | Viscosity | ASTM D445 |
| | Conradson Carbon | ASTM D189 or D4530 |
| | Salt | |

Step 1: Select Candidate Refineries which could Potentially Process the Target Crude Oil Not all crude oils are typically globally available. Therefore a determination is first made regarding which particular refineries are most likely to have accessibility to a given crude oil based on geography, transportation options and economics. In this example, the 2 target crudes to be analyzed are Ob River Light and Mondo. The refineries which are potentially interested in processing this crude are Refinery A and B due to current pricing, availability and operating envelopes. The key properties of interest are identified in Table 2.

TABLE 2

| | Crude Oils and Original Assayed Values | | | | |
|---|---|---|---|---|---|
| Grade | Origin | API Gravity | Sulfur, wt % | Nitrogen, ppm | Con Carbon, wt % |
| Ob River Light | Russia | 42 | 0.21 | 800 | 1.32 |
| Mondo | Angola | 30 | 0.25 | 2660 | 5.30 |

Step 2: Identify Key Refinery Processing Limitations

Refinery A is interested in potentially processing Ob River Light, however the sulfur, nitrogen and con carbon levels in the gas oil and resid portions of the stream are processing constraints. Refinery B is also interested in Ob River Light and Mondo, however the sulfur content of the crude and its distribution through the 600 degree F. plus region is of critical importance.

Step 3: Identify Target Crude Oil Qualities which May Generate Performance Issues Irrespective of any Given Refinery Additionally, there are numerous properties that can have a significant economic or operational impact on a refinery. Properties such as the total mercury level for crude oils susceptible to mercury contamination or the pour point for crudes which exhibit high pour point temperatures may also be of consequence. While these qualities typically cannot be distributed, they can be measured and the whole crude properties updated with current values for a given representative sample. The attached example will not address this specific situation since this is a simple case of the measuring the whole crude properties and distributing them through the boiling range.

Step 4: Identify Properties to be Measured for a Given Whole Crude Sample.

For Ob River Light, sulfur, nitrogen and Conradson carbon will be measured, while for Mondo only the sulfur will be a measured for distribution.

Distribution Value Priorities that should be Followed

Table 3 provides the typical refinery laboratory whole crude test capabilities, distribution selection priorities, approximate cost of the tests and approximate sample required. Even if a determination is made that all tests are required, they could be conducted at a modest cost of between $1,000 and $2,000 and require a modest sample size of less than 2 liters of the target crude oil.

TABLE 3

Typical Refinery Whole Crude Test Capability

| Analytical Test Description | Distribution Selection Priority ||| Approximate Cost, USD | Material Required (ml) |
| --- | --- | --- | --- | --- | --- |
| | Recommended Assay | Alternate Analytic Method | Whole Crude Measured | | |
| API | 3 | 2 | 1 | $ 25.00 | 50 |
| Sulfur | 3 | 2 | 1 | $ 25.00 | 20 |
| RVP | 2 | 3 | 1 | $ 30.00 | 100 |
| Salt | 2 | 3 | 1 | $ 40.00 | 50 |
| Ni | 2 | 3 | 1 | $ 20.00 | 10 |
| V | 2 | 3 | 1 | $ 20.00 | 10 |
| Fe | 2 | 3 | 1 | $ 20.00 | 10 |
| Na | 2 | 3 | 1 | $ 20.00 | 10 |
| Neutralization Number | 2 | 3 | 1 | $ 30.00 | 20 |
| H2S | 2 | 3 | 1 | $ 45.00 | 200 |
| Mercury | 2 | 3 | 1 | $300.00 | 50 |
| Conradson Carbon | 2 | 3 | 1 | $ 35.00 | 25 |
| Pour Point | 2 | 3 | 1 | $ 25.00 | 100 |
| Total Nitrogen | 3 | 2 | 1 | $ 75.00 | 10 |
| Mercaptan Sulfur | 3 | 2 | 1 | $ 45.00 | 200 |
| Viscosity @ 25 C. | — | — | 1 | $ 30.00 | 50 |
| Viscosity @ 40 C. | — | — | 1 | $ 30.00 | 50 |
| Viscosity @ 60 C. | — | — | 1 | $ 30.00 | 50 |
| Wax Content | 2 | 3 | 1 | $150.00 | 50 |

The distribution selection priority is used to guide which properties should be used when more than one critical property is available. In all cases the measured value should always be selected and the target crude values should be modified as described below to be consistent with the whole crude measured values. Whenever a whole crude measured value is not available, then a choice has to be made between using the value obtained from the alternate analytical techniques described above, or using the recommended assay value.

Depending upon the measurement reliability of the wet crude oil assay process and the prediction accuracy of the particular analytic method selected, a seriatim is established of which property should be used to model the final crude oil characterization. This particular seriatim is based on the alternative analytical methods described by J. M. Brown.

Adjusting the Distributed Properties Accordingly

The synthesized assays for the two target crudes were generated using the method of Brown (U.S. Pat. No. 6,662,116 B2, Dec. 9, 2003). FT-MIR spectra of the target crude samples were collected over the 5000-1000 cm$^{-1}$ range with the samples maintained at 65° C. API Gravity and kinematic viscosity at 40° C. were also measured. For the Mondo example, this data was analyzed relative to a library containing data for 530 reference crudes for which wet assay data was available. For the Ob River Light example, a larger library containing data for 562 crudes was used. The spectral data in the 4685.2-3450.0 cm$^{-1}$, 2238.0-1549.5 cm$^{-1}$ and 1340.3-1045.2 cm$^{-1}$ regions were orthogonalized to corrections for baseline, liquid water and water vapor, concatenated to the weighted data for linearly blendable data for API gravity and viscosity, and fit as a linear combination of similarly orthogonalized and concatenated data for reference crudes using a Nonnegative Linear Least Squares algorithm. $R^2$ is calculated as $$R^2 = 1 - \frac{\left(\left[\begin{array}{c}\hat{X}_u \\ w_{API}\hat{\lambda}_u(API) \\ w_{Visc}\hat{\lambda}_u(Visc)\end{array}\right] - \left[\begin{array}{c}SX_u \\ w_{API}\lambda_u(API) \\ w_{Visc}\lambda_u(Visc)\end{array}\right]\right)^T \left(\left[\begin{array}{c}\hat{X}_u \\ w_{API}\hat{\lambda}_u(API) \\ w_{Visc}\hat{\lambda}_u(Visc)\end{array}\right] - \left[\begin{array}{c}SX_u \\ w_{API}\lambda_u(API) \\ w_{Visc}\lambda_u(Visc)\end{array}\right]\right) / (f+2-c-1)}{\left(\left[\begin{array}{c}SX_u \\ w_{API}\lambda_u(API) \\ w_{Visc}\lambda_u(Visc)\end{array}\right] - \left[\begin{array}{c}SX_u \\ w_{API}\lambda_u(API) \\ w_{Visc}\lambda_u(Visc)\end{array}\right]\right)^T \left(\left[\begin{array}{c}SX_u \\ w_{API}\lambda_u(API) \\ w_{Visc}\lambda_u(Visc)\end{array}\right] - \left[\begin{array}{c}SX_u \\ w_{API}\lambda_u(API) \\ w_{Visc}\lambda_u(Visc)\end{array}\right]\right) / (f+2-1)} \quad [1]$$

$\lambda_u(api)$ and $\lambda_u(visc)$ are the volumetrically blendable forms of API and viscosity, and $w_{API}$ and $w_{visc}$ are the weighting factors for the two inspections. $\hat{\lambda}_u(api)$ and $\hat{\lambda}_u(visc)$ are the estimated blendable forms of API and viscosity calculated based on the Virtual Blend.

A Fit Quality, FQ, is calculated as:

$$FQ = \sqrt{1-R^2} \quad [2]$$

The Fit Quality Ratio, FQR, is calculated as:

$$FQR = \frac{FQ}{FQC} \quad [3]$$

FQC is a Fit Quality Cutoff. FQC is selected such that analyses with FQR≦1.0 will produce predictions of adequate precision for the intended application. Analyses for which FQR≦1.0 are referred to as Tier 1 analyses. For the library used in this example, FQC value of 0.0080 was selected such the precision of yield predictions for Tier 1 analyses is comparable to the reproducibility of the distillation. While the methodology of this invention preferably uses the results of Tier 1 analyses as input, Tier 2 analyses (FQR<1.5) are also used.

For the Mondo crude sample, a Tier 1 analysis with a FQR of 0.63 is obtained based on a blend of 15 reference crudes (Table 4). Despite the fact that the recommended assay is one of the library reference crudes, it is not included in the Virtual Blend, probably because of its significantly higher acid content. As expected for the Tier 1 analysis, the distillation yield predictions are within the reproducibility of the distillation procedure (Table 6). However, the sulfur analysis for the Mondo crude sample (0.25 wt %) is significantly lower than the value predicted by the Virtual Assay (0.38 wt %) suggesting that the sulfur distribution will also be off. Since sulfur content and it's distribution is critical to Refinery B, the methodology of this invention is used to recalculate the sulfur distribution for the Mondo target.

TABLE 4

Virtual Blend for Analysis of Mondo

| Grade | Location | Region | Volume % |
|---|---|---|---|
| ARUN CONDENSATE | Indonesia | Asia Pacific | 0.6 |
| CANO LIMON | Colombia | Latin America | 13.7 |
| COASTAL | California | U.S.A. | 4.5 |
| EAST SPAR | Carnevon Basin | Australia | 3.8 |
| LEGENDRE | Carnevon Basin | Australia | 4.1 |
| MARIMBA | Angola | Africa | 2.7 |
| MARLIM | Brazil | Latin America | 5.5 |
| MAVACOLA | Angola | Africa | 22.6 |
| PALANCA BLEND | Angola | Africa | 25.0 |
| PALANCA BLEND | Angola | Africa | 9.1 |
| QARUN | Egypt | Africa | 2.6 |
| SAKHALIN LIGHT | Sakhalin Island | Former Soviet Union | 0.6 |
| SAN JOAQUIN VALLEY | California | U.S.A. | 1.8 |
| SENIPAH CONDENSATE | Indonesia | Asia Pacific | 2.9 |
| WIDURI | Indonesia | Asia Pacific | 0.6 |

TABLE 5

Virtual Assay Results for Mondo

| | Recommended Assay | Virtual Assay | New Wet Assay |
|---|---|---|---|
| Crude | | | |
| API Gravity, | 27.9 | 34.85 | 34.8 |
| Viscosity at 40 C./104 F., cSt | 14.32 | 6.24 | 6 |
| Sulfur, wt % | 0.46 | 0.38 | 0.25 |
| Nitrogen (wt %), wt % | 0.29 | 0.202 | 0.22 |
| CCR, wt % | 6.2 | 3.69 | 3.59 |
| Neutralization number (TAN), MG/GM | 0.97 | 0.28 | 0.4 |
| Cut volume, % | | | |
| LVN (IBP-160 F.) | 5.61 | 8.11 | 8.83 |
| MVN (160-250 F.) | 6.98 | 9.1 | 8.45 |
| HVN (250-375 F.) | 11.17 | 12.55 | 12.8 |
| KERO (320-500 F.) | 16.41 | 18.15 | 17.4 |
| JET (360-530 F.) | 15.61 | 17.32 | 16.29 |
| DIESEL (530-650 F.) | 11.33 | 12 | 12.52 |
| LTGO (530-700 F.) | 15.96 | 16.74 | 16.75 |
| LVGO (700-800 F.) | 8.63 | 8.92 | 8.47 |
| MVGO (800-900 F.) | 7.57 | 7.75 | 8.34 |
| HVGO (900-1050 F.) | 9.52 | 8.51 | 8.04 |
| AtmRes (650+ F.) | 50.66 | 42.39 | 42.57 |
| VacRes (1050+ F.) | 20.31 | 12.47 | 13.49 |

For the Ob River Light crude sample, a Tier 2 fit is obtained with an FQR of 1.48 based on a Virtual Blend of 14 reference crudes (Table 6). This relatively poor fit indicates that the current sample is appreciably different from all reference crudes in the library including the Ob River Heavy reference. While the distillation yield predictions are not expected to be within the reproducibility of the distillation process, the yield predictions are still a significantly better estimate of composition than using the Ob River Heavy recommended assay (Table 7). The sulfur, nitrogen and Conradson carbon predictions from the Tier 2 fit are not adequate and must be improved using the methodology of this invention.7

TABLE 6

Virtual Blend for Analysis of Ob River Light

| Grade | Location | Region | Volume % |
|---|---|---|---|
| CHAMPION | Brunei | Asia Pacific | 0.8007 |
| EAST TEXAS SWEET | Texas | U.S.A. | 0.6583 |
| GIPPSLAND | Bass Strait | Australia | 3.0704 |
| HYDROTREATED SHALE NAPHTHA | Queensland | Australia | 5.1893 |
| KAJI-SEMOGA | Indonesia | Asia Pacific | 7.0745 |
| KOME | Chad | Africa | 0.1113 |
| LABUAN | Malaysia | Asia Pacific | 2.2229 |
| LAMINARIA | Timor Sea | Australia | 11.9891 |
| OB RIVER HEAVY | Russia | Former Soviet Union | 2.4487 |
| OSO CONDENSATE | Nigeria | Africa | 5.8753 |
| ROZEWIE | Poland | Europe | 0.2968 |
| SAN SEBASTIAN | Argentina | Latin America | 0.8082 |
| SIBERIAN LIGHT | Russia | Former Soviet Union | 55.2498 |
| YME | Norway | Europe | 4.2046 |

TABLE 7

Virtual Assay Results for Ob River Light

| | Recommended Assay | Virtual Assay | New Wet Assay |
|---|---|---|---|
| Crude | | | |
| API Gravity, | 32.3 | 40.88 | 41.8 |
| Viscosity at 40 C./104 F., cSt | 5.18 | 2.82 | 2.06 |
| Sulfur, wt % | 0.0945 | 0.3683 | 0.2089 |
| Nitrogen (wt %), wt % | 0.049 | 0.092 | 0.08 |
| CCR, wt % | 1.9 | 2.06 | 1.11 |
| Neutralization number (TAN), MG/GM | 0.07 | 0.08 | 0.05 |
| Cut volume, % | | | |
| LVN (IBP-160 F.) | 6.45 | 14.02 | 12.76 |
| MVN (160-250 F.) | 7.89 | 12.66 | 12.34 |
| HVN (250-375 F.) | 9.71 | 15.24 | 16.33 |
| KERO (320-500 F.) | 18.15 | 19.65 | 21.68 |
| JET (360-530 F.) | 19.53 | 18.01 | 20.13 |
| DIESEL (530-650 F.) | 19.07 | 10.88 | 13.22 |
| LTGO (530-700 F.) | 25.38 | 14.84 | 17.86 |
| LVGO (700-800 F.) | 10.58 | 7.19 | 7.2 |
| MVGO (800-900 F.) | 8.83 | 5.92 | 5.79 |
| HVGO (900-1050 F.) | 7.12 | 6.13 | 5.45 |
| AtmRes (650+ F.) | 38.6 | 30.89 | 27.1 |
| VacRes (1050+ F.) | 5.76 | 7.68 | 4.02 |

The Virtual Assay predicted distributions for these properties are modified in the following manner:
   In each case, a surrogate crude is selected to represent the expected shape of the property distribution. In these examples, the recommended assay is used as the surrogate for both Mondo and Ob River Light.
   Ideally, if it is within the capability of the assay workup tool, the property distribution curve for the surrogate crude is scaled up or down by a multiplication factor. The value of the factor is adjusted so as to obtain material balance for the property. The surrogate property distribution curve is multiplied by the corresponding yield curve (volume % yield for volumetric properties and weight % yield for weight based properties such as those in the example) and integrated to estimate the property value for the whole sample. The scaling factor is adjusted until the estimate agrees with the measured property.

Alternatively, if the assay workup tool does not have this capability, it may be necessary to use the surrogate crude assay to estimate property values for discrete distillation cuts over the entire boiling range. The distillation cuts for which the property is estimated would correspond to those for which the property is normally measured in the wet assay. The property values for these discrete cuts are then scaled up or down by a factor, and used to regenerate a new property distribution curve following the procedure normally used for assay data workup. The integral of the product of the property and yield curves is again checked against the measured whole crude property value for the target, and the scaling factor is adjusted to achieve material balance.

Table 8 through 11 summarizes the various property values for Ob River Light and Mondo as determined from the workups depicted in FIGS. 1 through 4. In each case, a new wet assay was done on the target crude sample as a check on the distribution modification methodology.

TABLE 8

Sulfur Distribution (wt %) for Ob River Light

|  | 343° C.+ | Whole Crude |
|---|---|---|
| Recommended Assay | 0.180 | 0.095 |
| VA Predicted Assay | 0.905 | 0.378 |
| Redistributed Assay | 0.506 | 0.209 |
| New Wet Assay | 0.557 | 0.209 |

TABLE 9

Nitrogen Distribution (ppm) for Ob River Light

|  | 343° C.+ | Whole Crude |
|---|---|---|
| Recommended Assay | 1136 | 490 |
| VA Predicted Assay | 2541 | 945 |
| Redistributed Assay | 2241 | 800 |
| New Wet Assay | 2305 | 800 |

TABLE 10

Conradson Carbon Distribution (wt %) for Ob River Light

|  | 343° C.+ | Whole Crude |
|---|---|---|
| Recommended Assay | 4.25 | 1.90 |
| VA Predicted Assay | 5.71 | 1.32 |
| Redistributed Assay | 3.08 | 1.11 |
| New Wet Assay | 3.49 | 1.11 |

TABLE 11

Sulfur (wt %) Distribution for Mondo

|  | 343° C.+ | Whole Crude |
|---|---|---|
| Recommended Assay | 0.745 | 0.46 |
| VA Predicted Assay | 0.718 | 0.36 |
| Redistributed Assay | 0.471 | 0.25 |
| New Wet Assay | 0.459 | 0.25 |

The recommended assay is the current assay that is considered to be the best representation of current quality of a crude oil grade based on previous data. The VA Predicted Assay is the updated estimate based on analytical and mathematical techniques to update a grade, in this case the methodology of Brown. The Redistributed Assay is the VA Predicted Assay that was modified by the techniques of this invention. The Wet Assay is a complete laboratory analysis of the same target sample used as the basis for the VA Predicted Assay and the Redistributed Assay that was performed to test the accuracy of this methodology.

Tables 12 and 13 provide a summary of the change in accuracy in predicting cut properties associated with this technique. Table 12—Per Cent Change to Wet Assay summarizes the percentage difference between the Recommended Assay, VA Predicted and Redistributed Assay to the actual measured Wet Assay. Table 13—Absolute change to Wet Assay summarizes the absolute value of the differences between the Recommended Assay, VA Predicted and Redistributed Assay to the actual measured Wet Assay.

TABLE 12

Per Cent Change to Wet Assay
Per Cent Change = (Selected Method Value − Wet Assay Value)/Selected Method Value

|  | 343° C. cut property values | | |
|---|---|---|---|
|  | Recommended Assay - Wet | VA Predicted Assay - Wet | Redistributed Assay - Wet |
| Sulfur - Ob River Light | −209% | 38% | −10% |
| Nitrogen - Ob River Light | −103% | 9% | −3% |
| CCR - Ob River Light | 18% | 39% | −13% |
| Sulfur - Mondo | 38% | 56% | 3% |

TABLE 13

Absolute Change to Wet Assay
Absolute Change = (Selected Method Value − Wet Assay Value)/Selected Method Value

|  | 343° C. cut property values | | |
|---|---|---|---|
|  | Recommended Assay - Wet | VA Predicted Assay - Wet | Redistributed Assay - Wet |
| Sulfur - Ob River Light | −0.377 | 0.348 | −0.051 |
| Nitrogen - Ob River Light | −1169 | 236 | −64 |
| CCR - Ob River Light | 0.76 | 2.22 | −0.41 |
| Sulfur - Mondo | 0.286 | 0.259 | 0.012 |

These tables clearly show that for every property which as been modified by the methodology of this invention, the redistributed assay results (Redistributed Wet Assay) for the critical 343° C. cut are significantly closer to the new wet assay results which were directly measured. These differences would have a material impact on crude purchase decisions and a significant economic delta in value.

The methodology for modifying a direct blended or closest match assay is as follows:
1. Create the Virtual Assay (target assay) as a function of the particular mathematical or analytic technique employed, preferably the methodology of Brown (U.S. Pat. No. 6,662,116 B2, Dec. 9, 2003), herein referred to as EM Virtual Assay.
2. Import the values of the target assay generated by this technique into an assay workup program. The assay workup program is typically used to import measured laboratory data generated during the execution of a wet crude assay, and is used to curve fit, smooth and distribute measured properties throughout the boiling range of the crude oil. The result of the assay workup process is a completed, material balanced assay with full property distributions that can then be used for business decisions as shown in FIGS. 1 through 4.
3. Determine which crude will be used as a surrogate crude for the target assay to provide a basis for property distribution. It is recognized that crude oils sharing similar physical and or chemical characteristics will have their properties distributed in a similar fashion as a function of boiling point. The best selection of a surrogate is a crude oil of the same grade, based on an earlier wet crude oil assay. While the absolute values may differ, crude oils sharing these characteristics will also exhibit similar property distributions. If a wet crude oil assay is not available to be selected as a surrogate, then selecting a crude based on similar physical, chemical or geological family is the next best alternative.
4. Import the surrogate crude oil assay into the assay workup tool.
5. Modify the distribution of the selected property in the target assay (sulfur, nitrogen and Conradson carbon in the attached figures, but this approach works equally well for any distributed property) per the distribution exhibited by the surrogate assay which as based on an actual measured wet crude oil assay.
6. Adjust the distributed curve for the target assay to ensure the overall level of sulfur present in the entire crude oil matches the measured value obtained from the target crude. If possible, scale the entire distribution curve such that the integral of the product of the distribution and yield curves agrees with the measured property value. Alternatively, use the curve for the surrogate crude to estimate property data for those distillation cuts for which the property would be measured in a wet assay, scale these estimated property values, refit these scaled values via the normal assay workup procedure to obtain a new property distribution curve, and check that the integral of the product of the property and yield curves match the measured property value for the target. Adjust the scaling factor used to achieve material balance.
7. Repeat the procedure for all other properties that have been measured and require adjustment. For the Ob River Light example provided, sulfur, nitrogen and Conradson carbon would be adjusted. While it may be typically expected that the same surrogate crude oil would be selected to be used as a basis for adjusting the target assay values, different surrogate crude oils could be selected if it is determined they better model the particular property distribution.

Ensuring the Final Modified Blended Assay is in Material Balance.

8. Care must be exercised to ensure that all properties properly material balance. While the above process ensures the sum of the distributed properties equals the measured whole crude value, other inter-related properties must be checked as well.
9. Inter-related properties include, but are not limited to total sulfur and aliphatic sulfur, nitrogen and basic nitrogen, and particular metal value versus the total metals in the crude. It is obvious that a specialized chemical form of sulfur or nitrogen cannot exceed the total sulfur or nitrogen present in a crude oil. Therefore, adjustments must be made to ensure the crude oil distributions are material balanced. Therefore, other inter-related properties should be proportionately adjusted in the target crude to match the relationship exhibited in the surrogate crude oil.
10. Save the adjusted target crude oil values and export to the crude assay database for use as with other crude oil assays.

The advantage of this invention is a resulting assay, which captures the benefits of the faster and less expensive analytical techniques that are now available, but still maintain the high quality and accuracy of critical values in the assay. Providing an accurate analysis is important to feedstock selection to ensure optimal crude oil valuation and selection. As previously explained, differences in sulfur, as an example, of as little as 100 to 200 ppm in the diesel cut, could have economic consequences of well over $250,000 per purchased cargo. Accurately determining these values translates into a major economic credit when purchasing crude oil in large volumes typical of large crude carriers.

Additionally, exceeding refinery limitations for critical values has an impact beyond proper economic valuation for purchase. A refinery may purchase a crude oil cargo expecting a sulfur value of 1% sulfur based on the quick analytic techniques described. This particular refinery may have a limitation on feed sulfur of 1% due to refinery configuration and product specifications. If the purchased crude oil arrives with a value of 1.5% sulfur, then the refinery must purchase an extremely low sulfur crude oil at an economic premium to blend the feed sulfur levels back to a 1% target. This can result in an economic loss or limited processing options to rundown the high sulfur purchase. Accurate characterization of the feedstock is important from an economic, operability and safety standpoint.

Figure 1:
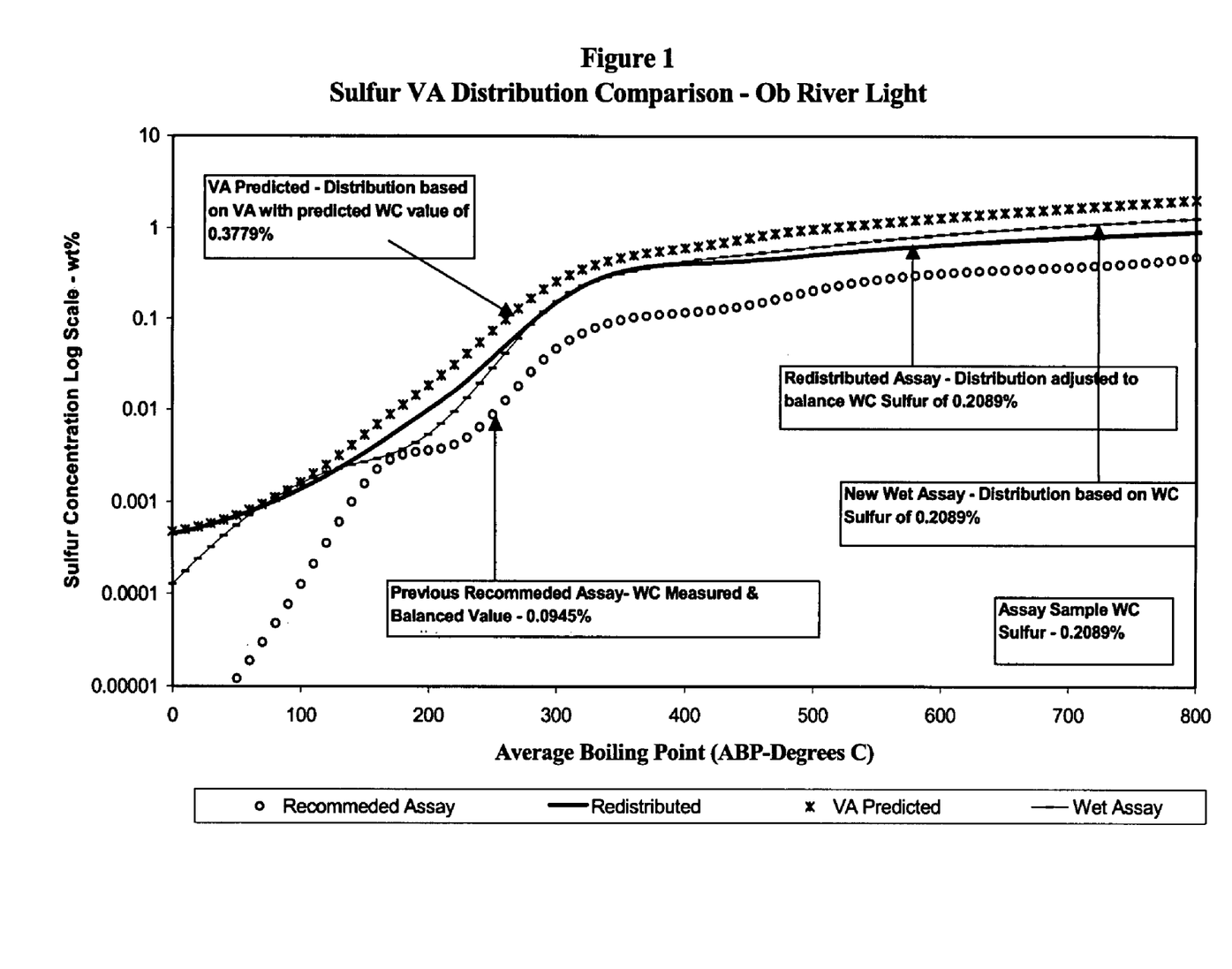
FIG. 1 shows the sulfur distribution for Ob River Light.
Figure 2:
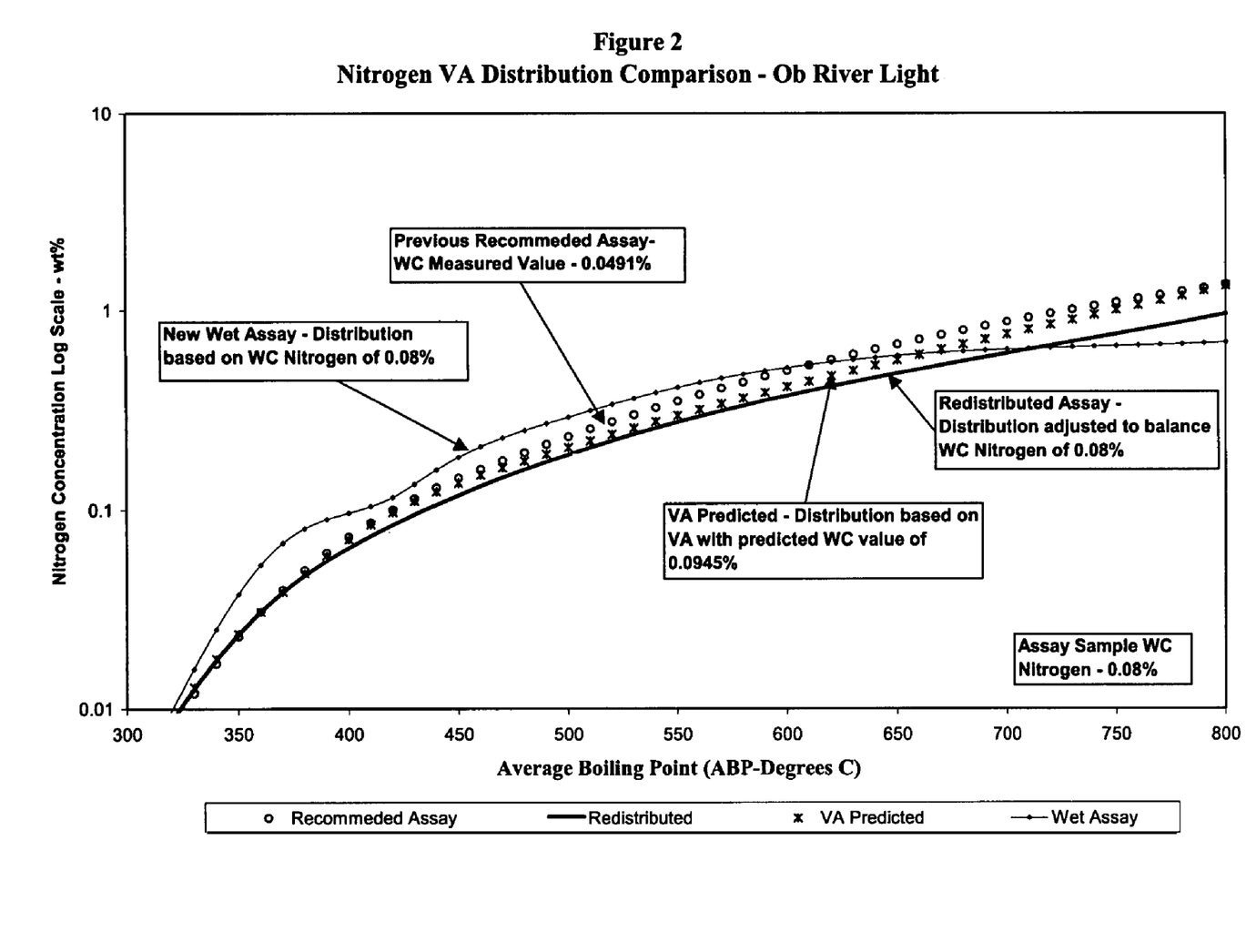
FIG. 2 shows the nitrogen distribution for Ob River Light.
Figure 3:
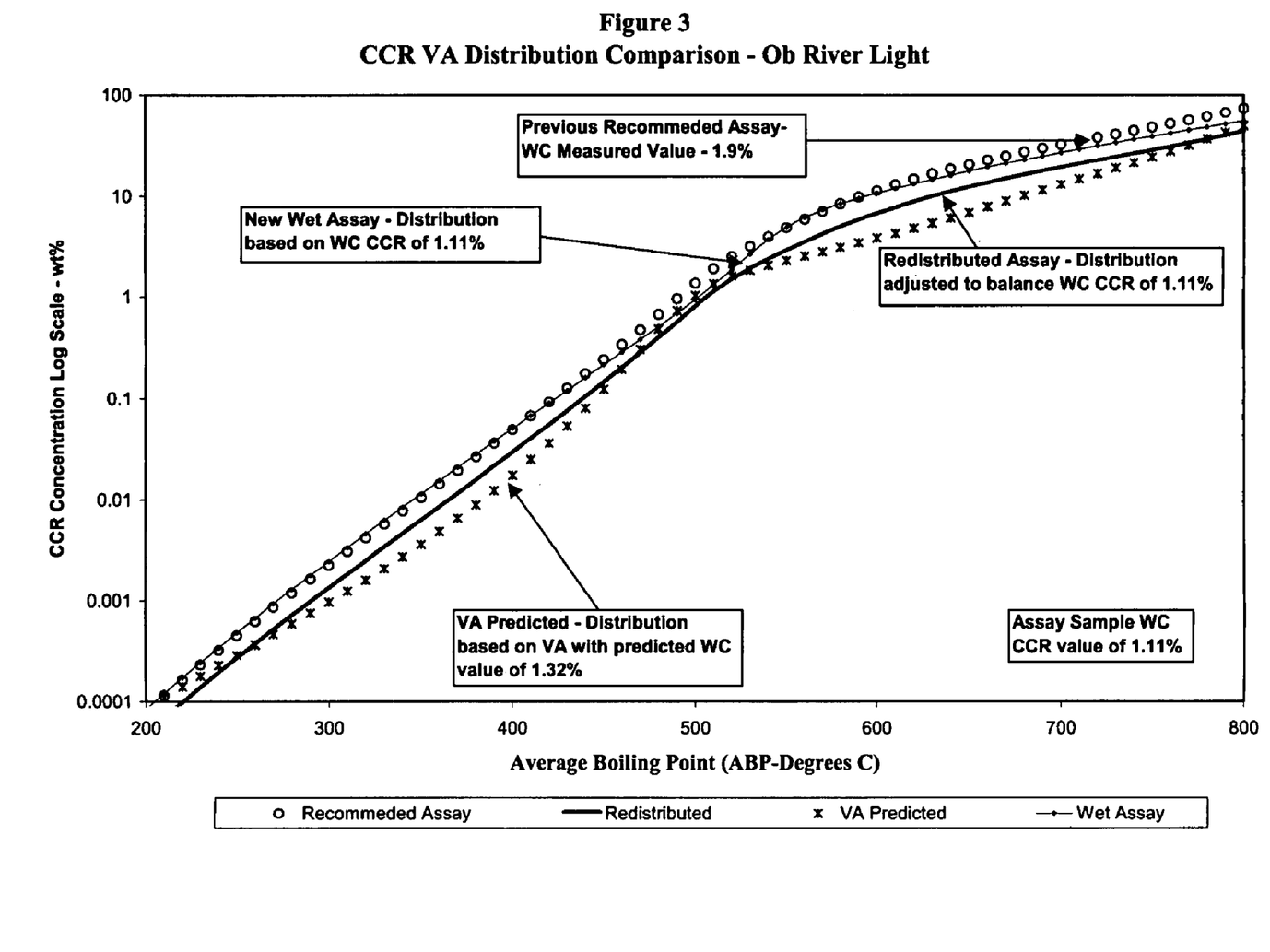
FIG. 3 shows the Conradson Carbon Distribution for Ob River Light.
Figure 4:
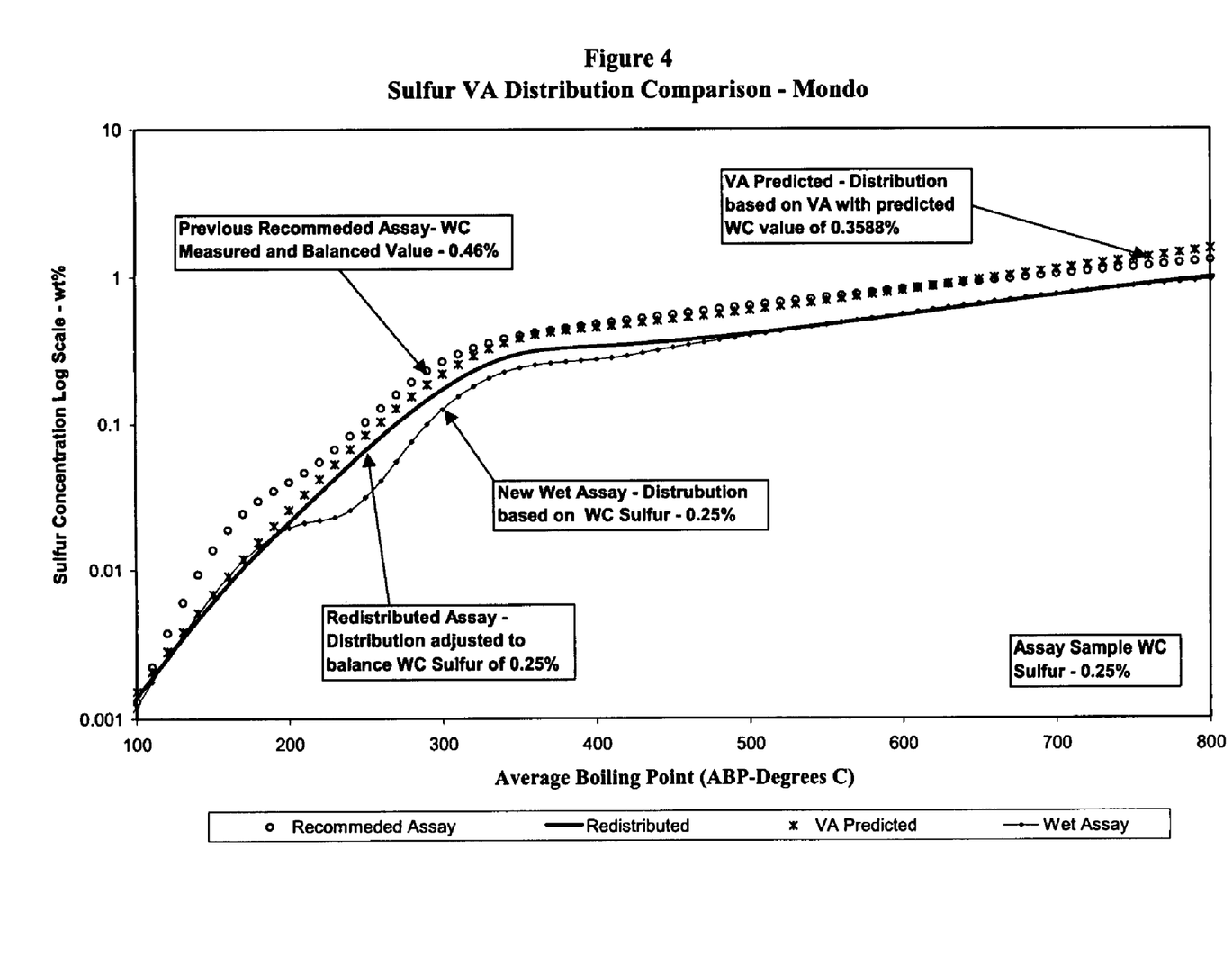
FIG. 4 shows the sulfur distribution for Mondo.

For FIGS. 1 though 4, the following terminology applies.
1. Recommended Assay—current assay of a given grade which is being used to represent the current crude quality.
2. VA Predicted—The quality that is predicted by the approach identified by EM virtual assay.
3. Redistributed—The property curve that results after measuring the whole crude property of interest and redistributing it per previous assay curves.
4. Wet Assay—The new assay that results from a complete assay performed on the grade of crude comparable to the redistributed assay.

What is claimed is:
1. A method for generating an assay of an unknown material including a whole crude oil or a portion of a whole crude oil comprising:
 a) generating a synthetic assay of the unknown material which provides distillation yield as a function of boiling point, wherein said synthetic assay is generated by the steps of determining an IR spectrum of said material, fitting said IR spectrum to a linear combination of known IR spectra in a database to determine the coeffi- cients of the linear combination, wherein the database includes IR spectra of reference crude oils whose distillation yield as a function of boiling point are known, and determining the distillation yield as a function of boiling point of said material from the coefficients of the linear combination and the boiling range fraction yields of the reference crudes, b) measuring one or more critical property of the unknown material, c) selecting a known surrogate assay for each of the critical properties to provide a property distribution for each critical property wherein said property distribution is a function of boiling point, d) calculating a material balanced value for each critical property which gives the total amount of the critical property in said unknown material, e) adjusting the property distributions from step c) such that the material balanced property values equal the measured property values from step b), f) replacing the property distributions of the synthetic assay with the adjusted property distributions of step e).

2. The method of claim 1 wherein the unknown material is a crude oil, a condensate or a resid.

3. The method of claim 1 wherein the critical property is selected from the group consisting of API gravity (American Petroleum Institute), Sulfur, RVP (Reid Vapor Pressure), Salt, Ni, V, Fe, Na, and neutralization Number.

4. The method of claim 3 wherein said critical property is API gravity.

5. The method of claim 3 wherein said critical property is Sulfur.

6. The method of claim 3 wherein said critical property is Neutralization Number.

* * * * *